United States Patent
McGuckin, Jr.

(10) Patent No.: US 6,293,927 B1
(45) Date of Patent: Sep. 25, 2001

(54) STATIONARY CENTRAL TUNNEL DIALYSIS CATHETER WITH OPTIONAL SEPARABLE SHEATH

(75) Inventor: James F. McGuckin, Jr., Radnor, PA (US)

(73) Assignee: Rex Medical, Radnor, PA (US)

( * ) Notice: Subject to any disclaimer, the term of this patent is extended or adjusted under 35 U.S.C. 154(b) by 0 days.

(21) Appl. No.: 09/122,186

(22) Filed: Jul. 23, 1998

Related U.S. Application Data (60) Provisional application No. 60/053,662, filed on Jul. 24, 1997.

(51) Int. Cl.$^7$ .............................. A61M 25/00; A61M 5/32
(52) U.S. Cl. ........................ 604/266; 604/264; 604/523; 604/508
(58) Field of Search .................. 604/43, 523, 530, 604/96, 161, 164, 264, 266, 268, 160, 524; 607/123

(56) References Cited

U.S. PATENT DOCUMENTS

| | | | |
|---|---|---|---|
| 3,938,530 | * | 2/1976 | Santomieri ........................ 128/349 |
| 4,166,469 | * | 9/1979 | Littleford ......................... 128/784 |
| 4,403,983 | | 9/1983 | Edelman et al. . |
| 4,451,252 | | 5/1984 | Martin . |
| 4,493,696 | | 1/1985 | Uldall . |
| 4,543,087 | | 9/1985 | Sommercorn et al. . |
| 4,568,329 | | 2/1986 | Mahurkar . |
| 4,583,968 | | 4/1986 | Mahurkar . |
| 4,619,643 | * | 10/1986 | Bai ...................................... 604/43 |
| 4,623,327 | | 11/1986 | Mahurkar . |
| 4,643,711 | | 2/1987 | Bates . |
| 4,682,978 | | 7/1987 | Martin . |
| 4,738,667 | | 4/1988 | Galloway . |
| 4,808,155 | | 2/1989 | Mahurkar . |
| 4,808,163 | * | 2/1989 | Laub .................................. 604/105 |
| 4,950,259 | | 8/1990 | Geary et al. . |
| 4,968,307 | | 11/1990 | Dake et al. . |
| 4,981,477 | | 1/1991 | Schon et al. . |
| 5,009,636 | | 4/1991 | Wortley et al. . |
| 5,053,022 | | 10/1991 | Martin . |
| 5,057,073 | | 10/1991 | Martin . |
| 5,104,388 | * | 4/1992 | Quackenbush ................... 604/264 |
| 5,122,125 | | 6/1992 | Deuss . |
| 5,156,592 | | 10/1992 | Martin et al. . |
| 5,167,623 | | 12/1992 | Cianci et al. . |
| 5,209,723 | * | 5/1993 | Twardowski et al. ............. 604/43 |
| 5,209,742 | * | 5/1993 | Venema et al. ................... 604/281 |
| 5,215,527 | | 6/1993 | Beck et al. . |
| 5,221,255 | | 6/1993 | Mahurkar et al. . |
| 5,221,256 | | 6/1993 | Mahurkar . |
| 5,246,430 | | 9/1993 | MacFarlane . |
| 5,346,471 | | 9/1994 | Raulerson . |
| 5,348,536 | | 9/1994 | Young et al. . |
| 5,350,358 | | 9/1994 | Martin . |

(List continued on next page.)

FOREIGN PATENT DOCUMENTS

| | | |
|---|---|---|
| 0386408 | 9/1990 | (EP) . |
| 440992 A2 | 8/1991 | (EP) . |

Primary Examiner—Richard K. Seidel
Assistant Examiner—Jennifer Maynard

(57) ABSTRACT

A stationary central dialysis catheter having a planar axially elongated sinuous tubular member having a plurality of axially extending lumens therein and at least a part having a predetermined two-dimensional shape including at least two portions of relative straightness connected by a curved portion region. At least two of said lumens each have at least one aperture for passage of fluid during dialysis, and said apertures are axially displaced from one another along said tubular member. A flexible sheath surrounding at least a part of the tubular member is peelably removable therefrom in situ. Ripcord means is provided in the form of a suture embedded in said flexible sheath and looped around at the distal portion to define a line of weakness separable first adjacent the suture loop for rupturing said sheath in a proximal direction.

30 Claims, 8 Drawing Sheets

U.S. PATENT DOCUMENTS

| | | |
|---|---|---|
| 5,360,397 | 11/1994 | Pinchuk . |
| 5,364,344 | 11/1994 | Beattie et al. . |
| 5,380,276 | 1/1995 | Miller et al. . |
| 5,403,291 | 4/1995 | Abrahamson . |
| 5,405,320 | 4/1995 | Twardowski et al. . |
| 5,445,625 * | 8/1995 | Voda .................................. 604/281 |
| 5,451,206 | 9/1995 | Young . |
| 5,472,417 | 12/1995 | Martin et al. . |
| 5,480,380 | 1/1996 | Martin . |
| 5,486,159 | 1/1996 | Mahurkar . |
| 5,489,278 | 2/1996 | Abrahamson . |
| 5,509,897 * | 4/1996 | Twardowski et al. ................. 604/43 |
| 5,509,900 | 4/1996 | Kirkman . |
| 5,556,390 | 9/1996 | Hicks . |
| 5,571,093 | 11/1996 | Cruz et al. . |
| 5,685,867 | 11/1997 | Twardowski et al. . |
| 5,718,678 | 2/1998 | Fleming, III . |
| 5,752,937 * | 5/1998 | Otten et al. .......................... 604/161 |
| 5,772,693 * | 6/1998 | Brownlee ............................. 607/123 |
| 5,779,669 | 7/1998 | Haissaguerre et al. ................ 604/95 |
| 5,792,123 | 8/1998 | Ensminger . |
| 5,800,384 | 9/1998 | Russell et al. . |
| 5,807,311 | 9/1998 | Palestrant . |
| 5,807,329 | 9/1998 | Gelman ................................. 604/96 |
| 5,830,196 | 11/1998 | Hicks . |
| 5,916,209 * | 6/1999 | Mick .................................... 604/523 |
| 5,957,893 | 9/1999 | Luther et al. . |
| 5,976,103 | 11/1999 | Martin . |
| 5,976,120 | 11/1999 | Chow et al. . |
| 5,984,908 | 11/1999 | Davis et al. . |
| 6,001,079 | 12/1999 | Peurchez . |
| 6,013,068 | 1/2000 | Spiegelhalter . |
| 6,059,771 | 5/2000 | Balbierz et al. . |

* cited by examiner

STATIONARY CENTRAL TUNNEL DIALYSIS CATHETER WITH OPTIONAL SEPARABLE SHEATH

CROSS-REFERENCE TO RELATED PATENT APPLICATION

This patent application is based on and claims the benefit of the filing date of U.S. provisional patent application No. 60/053,662 filed Jul. 24, 1997 by James F. MCGUCKIN, Jr., M.D. and entitled "Stationary Central Axis Tunnel Catheter".

FIELD OF THE INVENTION

This invention relates to an implantable surgical device and method of delivery. More specifically, this invention provides a multiple lumen catheter and separable sheath for delivering the catheter to the arteriovenous system in order to perform hemodialysis.

BACKGROUND OF THE INVENTION AND DESCRIPTION OF THE PRIOR ART

Multiple lumen catheters which are surgically implanted into the body and used for dialysis are known, being disclosed in U.S. Pat. Nos. 5,405,320 and 5,509,897 to Twardowski et al. and U.S. Pat. No. 5,509,900 to Kirkman.

The multiple lumen catheters disclosed in '320 and '897 are three dimensional in form, specifically calling for catheter portions which are substantially perpendicular to remaining, planar portions. Such multiple lumen catheters have been promoted as being allegedly permanent devices providing access to a patient arteriovenous system for hemodialysis but have proven to have significant disadvantages. The three dimensional character of these catheters inherently serves to stress the vessels of the arteriovenous system in which the catheter resides, thereby shortening useful life of the catheter.

The catheter disclosed in '900 is intended and designed to be retained at a specific spot within a blood vessel by an anchoring tip which serves to retain the catheter with respect to the wall of the blood vessel. The anchoring tip, by fixing the catheter in place and not permitting relative movement of the vessel vis-a-vis the catheter, creates a potential for rupture of the vessel or for collection of thrombolytic material about the positioning means, both of which are undesirable.

With the increasing use of dialysis therapy and ever a increasing expected lives of dialysis patients, the need exists for a permanent dialysis catheter which can be surgically implanted within the patient's blood vessels, and causing minimum trauma to the patient on a continuing basis. The need further exists for such a catheter which minimizes the possible collection of thrombolytic material at the inlet and outlet orifices of the catheter while keeping the inlet and outlet orifices remote from the wall of the vessel in which the catheter resides, thereby promoting high flow hemodialysis with relatively low fluid pressures, resulting in minimal patient connection time to the dialysis machine, longer catheter useful life and reduced possibility of catheter dysfunction as a result of malpositioning.

Surgical cannulas or "sheaths" are typically utilized by medical personnel to establish transcutaneous access channels from a first percutaneous location to a second subcutaneous location. The access channel provides a conduit for the delivery of pharmaceutical products, removal of subcutaneous sample tissue and fluid, as well as the coaxial passage of instrumentation such as catheters and the like.

In surgical procedures which require only temporary use of a sheath conduit, "peel-away" style sheaths are utilized. The peel-away sheath has lines of weakness extending about opposing sides of its longitudinal length such that removal of the sheath can be accomplished by applying a separating force or "peeling" the wall sections downwardly from the transcutaneous end by way of integral pull tabs located thereon, to cause a linear tearing of the sheath material causing the "peeling" or failure of the A material. In this way, the sheath can be removed from the patient without removing the instruments positioned within the sheath channel.

However, application of the peeling force to the sheath wall sections tends to aggravate and/or enlarge the incision in the region of the sheath as force is applied downwardly into the incision. Stressing of the incision is particularly problematic in irregularly manufactured sheaths having uneven wall thickness along the lines of weakness. The wall thickness may also cause kinking when attempting to insert a product or device through its thin walls. Moreover, the peeling force tends to lift instruments within the sheath pathway upwardly from the patient.

SUMMARY OF THE INVENTION

In one of its aspects, this invention provides a stationary central tunnel dialysis catheter including a planar axially elongated sinuous tabular member having a plurality of axially extending lumens formed therein. At least a part of the tubular member may be of predetermined two-dimensional, generally M-shape in order to substantially match the human left side venous anatomy. The M-shape includes portions of relative straightness connected by curved portions and is adapted to fit in a preselected body lumen in the anatomical region of interest. The M-shaped part of the tubular member is preferably deformable, resiliently returning to the predetermined two-dimensional M-shaped after deformative surgical implantation in the patient by way of a separable sheath delivery system. The M-shape part of the tubular member preferably has at least two lumens, with each having at least one aperture separated from the other but proximate the extremity of a leg of the M for through passage of fluid during dialysis; the apertures are axially displaced one from another. In the M-shape configuration of the catheter, there are preferably at least four portions of relative straightness.

In yet another of its aspects, this invention provides a stationary central tunnel dialysis catheter including a planar axially elongated sinuous tubular member having a plurality of axially extending lumens formed therein. At least a part of the tubular member preferably has a predetermined two-dimensional shape substantially matching an anatomical central tunnel region of interest and preferably includes at least two portions of relative straightness connected by a curved portions, fitting a preselected body lumen in the anatomical region of interest. The tubular member is preferably deformable, resiliently returning to its predetermined two-dimensional shape after deformative surgical implantation in the patient.

In the part of the tubular member having predetermined shape, at least two of the lumens each have at least one aperture for through passage of fluid during dialysis with the apertures being axially displaced one from another along the tubular member.

The catheter may further optionally but preferably include a flexible sheath complementally surrounding at least the part of the tubular member having predetermined two-dimensional shape to facilitate delivery and aseptic protection thereof with the sheath being removable therefrom in situ when the tubular member has been positioned within the preselected lumen. When the flexible sheath is included as a part of the catheter, ripcord means preferably extends along the length of the tubular member for rupturing the sheath in the vicinity of an axial extremity of the tubular member proximate the apertures. The ripcord means extends in response to preferably manual force preferably applied to a portion of the ripcord extending from a body of the patient in whom the catheter has been implanted. The ripcord may be embedded in the tubular wall or may be inside the sheath or may be imbedded in the sheath.

This invention additionally provides a separable surgical sheath wherein the sheath is removed from the transcutaneous location and readily separated from the catheter positioned therein by percutaneously initiating separation of a length of the conduit from a first conduit wall location to a second conduit wall location. This allows for remote sheath removal and for the catheter to be delivered along with the sheath as a package, facilitating passage of the device into the patient's arteriovenous system for hemodialysis.

The sheath in accordance with the invention includes a conduit preferably having distal and proximate ends and a line of weakness extending about the longitudinal length of the conduit. The line of weakness is ruptured by a separation control. The conduit has a pre-formed line of weakness traversing its longitudinal length. The device preferably utilizes an embedded suture to define the line of weakness which is ruptured by the application of force to a free end of the embedded suture or ripcord. The tip of the embedded portion of the sheath may employ a stress concentration area to initiate predetermined failure such that embedded suture rupture begins along a predetermined end of the conduit.

In a preferred embodiment the embedded suture defines the weakened section of the conduit wall such that pulling the suture away from the wall separates the conduit wall along the line of weakness. The suture is embedded from the proximal end of the conduit downwardly to the distal end with a free end of the suture preferably looping at the distal end upwardly to the proximal end. In this way separation control is simply the free end of the suture maintained at a percutaneous location i.e., the distal end of the conduit. Drawing the suture upwardly, away from distal end of the conduit causes the conduit, to rupture along the suture path such that the sheath may be removed from its transcutaneous position. Alternatively, the suture may be configured to rupture the conduit wall beginning with the proximate end and proceeding toward the distal end depending on orientation of the free end of the suture and application of force thereto.

In yet another of its aspects, this invention provides a stationary dialysis catheter including a planar axially elongated sinuous tubular member of integral construction having a plurality of axially extending lumens formed therein and a generally rounded smooth outer periphery. At least two of the lumens each have at least one aperture for through passage of fluid during dialysis with the apertures being axially displaced one from another along the tubular member yet proximate one end of the tubular member. The tubular member preferably has predetermined two-dimensional shape substantially matching an anatomical central tunnel of interest and includes at least two portions of relative straightness connected by a curved portion region, to fit the preselected body lumen in the anatomical region of interest. The tubular member is preferably deformable, resiliently returning to the predetermined two-dimensional shape after deformation, i.e. implantation using the separable sheath, and includes means for separating the tubular member aperture remote from the end of the tubular member from the surrounding wall of the preselected body lumen when the catheter is in place therewithin while permitting axial movement of the tubular member within the lumen relative to the lumen wall.

The tubular member preferably has a generally oval crosssection. The oval periphery is preferably formed by a pair of parallel sides connected by opposed semi-circular arcs.

The vessel wall separating means preferably is an enlarged portion extending outwardly beyond one of the arc segments or outwardly beyond one of the parallel sides or both. The vessel wall separating means is preferably resiliently deformable, for example to within the periphery of the tubular member. The inlet and outlet apertures of the tubular member may face axially or radially or both.

In yet another of its aspects, the invention provides a stationary dialysis catheter including a tubular member of the type described above where the tubular member has wall thickness greater in the area of its curved portions than in the area of its straight portions to assist kinking. The tubular wall member thickness may be greater at an outer part of the curved portion than at a corresponding inner part of the curved portion.

Additional benefits and advantages of this invention will become apparent to those skilled in the art upon a reading and understanding of the following detailed specification and related drawings.

DESCRIPTION OF THE PREFERRED EMBODIMENTS

Figure 1:
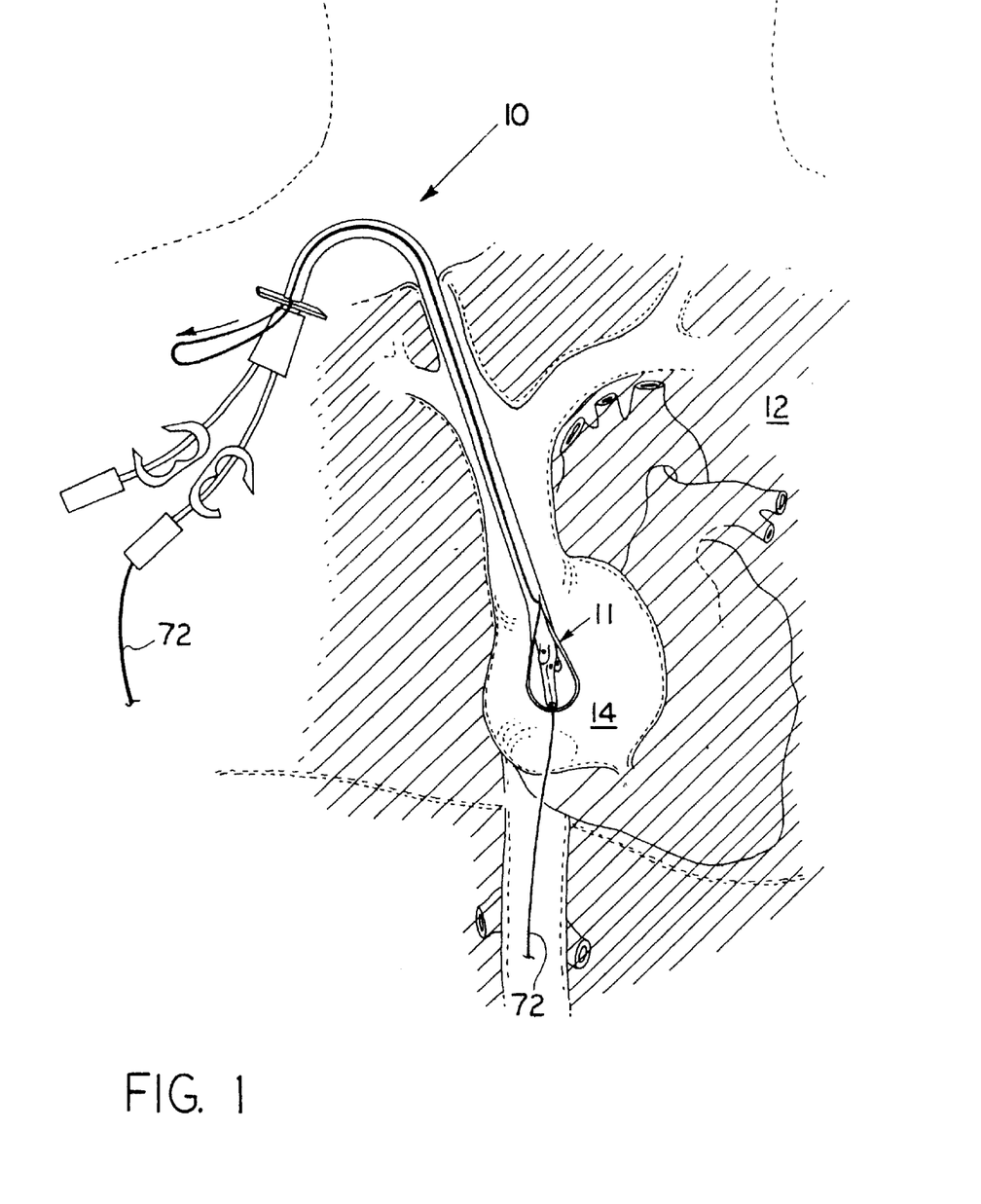
FIG. 1 is a schematic view illustrating a catheter embodying aspects of the invention in position in the right venous cavity of a human body.
Figure 8:
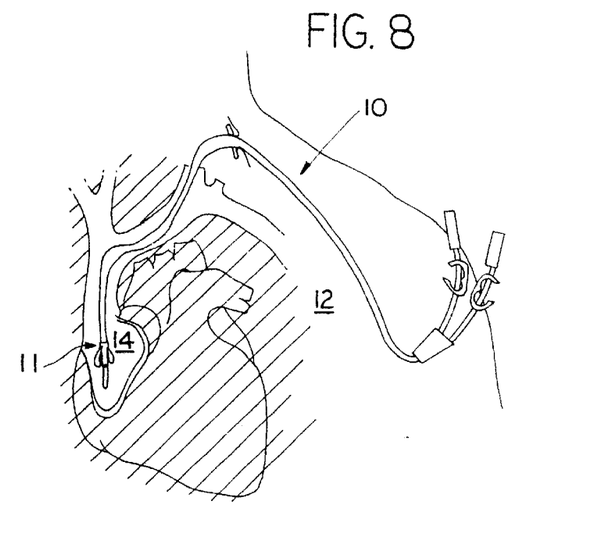
FIG. 8 is a schematic view illustrating a catheter embodying aspects of the invention in position in the left venous cavity of a human body.
Figures 9, 10, 11:
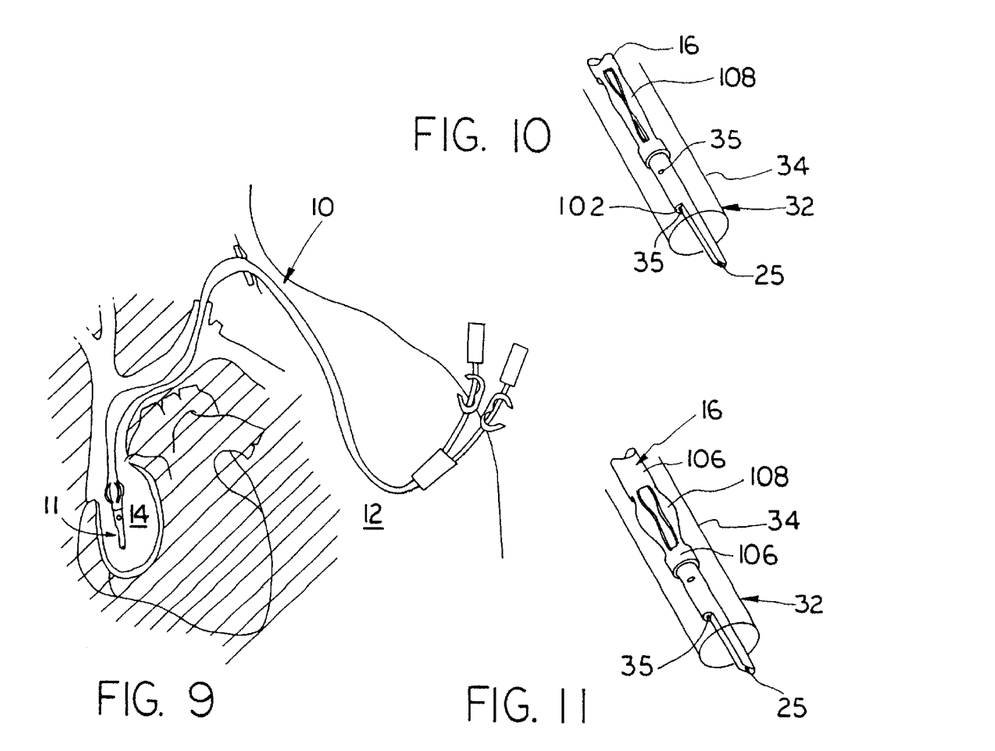
FIG. 9 is a view similar to FIG. 8 but illustrating a different enlarged tip configuration at the in situ end of the tubular member.
FIG. 10 is a view similar to FIG. 7 but illustrating a different configuration of the enlarged tubular tip member in situ.
FIG. 11 is a view similar to FIG. 7 but illustrating yet a still different configuration of the tubular member enlarged in situ.

A stationary central tunnel dialysis catheter in accordance with the invention is illustrated in FIGS. 1, 8 and 9 positioned in the thoracic cavity of the body where the catheter is designated generally 10. FIG. 1 illustrates the catheter in position on the right side of the body; FIGS. 8 and 9 depict a catheter implanted in the left side of the body.

Catheter 10 is formed as a planar axially elongated sinuous tubular member of integral construction. The tubular member is designated generally 16 and has a plurality of axially extending lumens formed therein and a generally rounded, smooth outer periphery. The preferred configuration of tubular member 16 is illustrated in cross-section in FIGS. 5 and 6 where the rounded, smooth exterior of tubular member 16 is apparent.

Tubular member 16 includes at least one intake lumen for inflow of blood out of the patient to a dialysis apparatus and a discharge lumen where discharge of blood which has been dialyzed back into the patient. The discharge lumen is designated generally 15 in the drawing; the intake lumen is designated generally 20.

Figure 2:
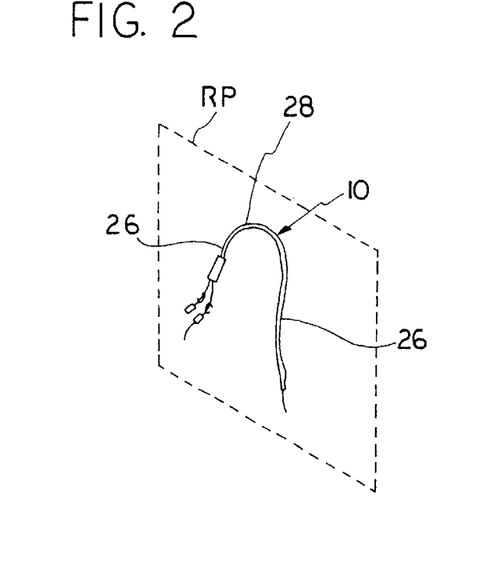
FIG. 2 is a schematic view illustrating the planar nature of the catheter embodying aspects of the invention as illustrated in FIG. 1.
Figure 3:
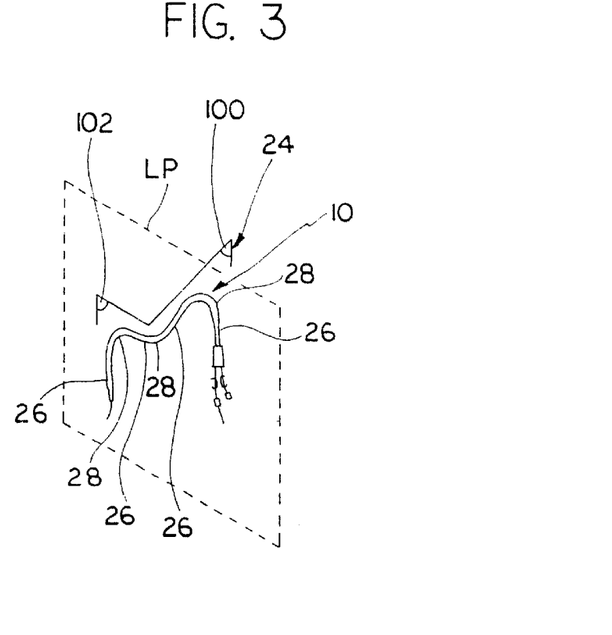
FIG. 3 is a schematic view illustrating the planar nature of a catheter embodying aspects of the invention and being formed in a generally M-shaped to fit in the left venous cavity of the body.

The planar catheter 10, whether installed in the left portion of the body or the right-hand portion of the body, is depicted in FIGS. 2 and 3 where planes have been depicted in dotted lines with the catheter 10 resident within the plane, to illustrate such planar character. FIG. 2 illustrates the catheter when configured for the right side; FIG. 3 illustrates the catheter when configured for the left side. In either case tubular member 16 of catheter 10 has a predetermined two-dimensional shape substantially matching an anatomical central tunnel region of interest. From FIGS. 2 and 3, it may be seen that in both instances catheter 10 includes at least two portions of relative straightness which are connected by a curved region; the shapes illustrated fit preselected body lumens in the anatomical regions of interest.

Tubular member 16 of catheter is deformable and has a memory characteristic so that when deformed, tubular member 16 resiliently returns to the predetermined two-dimensional shape upon deformation. Hence, when the catheter is installed in the body, while the catheter may be deformed from the predetermined shape, once resident in the selected lumen of the body, the catheter returns to its predetermined shape due to the memory characteristic. With the catheter assuming the predetermined shape, this contributes to comfort for the patient and minimal trauma to the arteries in which the catheter resides.

Figure 4:
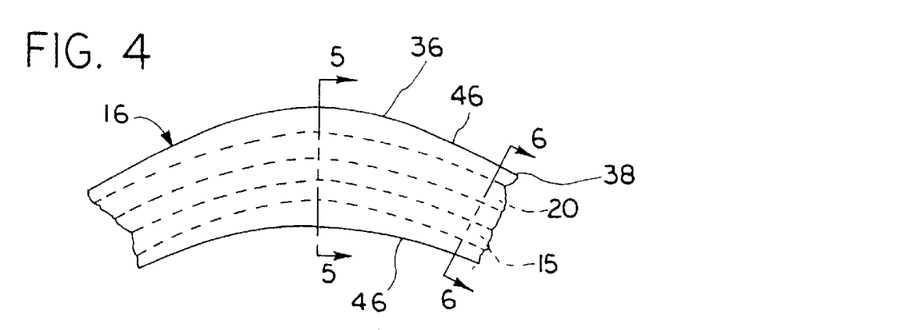
FIG. 4 is a broken view of a tubular member forming a portion of a catheter embodying aspects of the invention.
Figure 5:
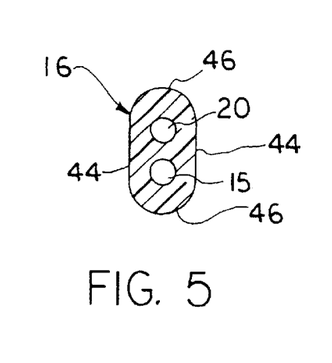
FIG. 5 is a sectional view taken at arrows 5—5 in FIG. 4.
Figure 6:
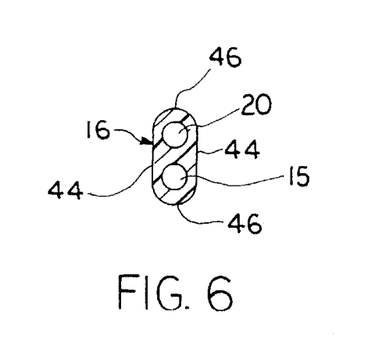
FIG. 6 is a sectional view taken at arrow 6—6 in FIG. 4.

As apparent from FIGS. 5 and 6, tubular member 16 preferably has a generally oval cross-section. The oval has a pair of parallel sides connected by opposed semi-circular arc segments. As apparent from FIGS. 4, 5 and 6, curved portions of tubular member 16, which curved portions are denoted generally 36, have greater wall thickness, as illustrated in FIG. 5, then straight portions of tubular member 16 as designated generally 38.

As apparent from FIGS. 3, 8 and 9, when catheter 10 is the left side of thoracic cavity 12, catheter 10 assumes a generally M-shape as indicated 24 in FIG. 3 where straight lines have been drawn as extensions of the straight line portions of catheter 10 to emphasize the M-shape when catheter 10 is installed on the left side of the body. The interior angles of the M-shape indicated as 100 and 102 in FIG. 3 can desirably vary from about 45° to as great as 120°; angles in the neighborhood of 45° to 60° are most common and are preferred.

In any of its embodiments catheter 10 includes means for separating the inlet aperture for intake lumen 20 from the wall 34 of a surrounding vessel in which catheter 10 is installed.

FIGS. 7, 10, 11 and 14 through 23 depict various embodiments of the means for separating tubular member aperture 20 from the vessel wall 34. In FIGS. 7, 10 and 11 through 23, the outlet aperture of discharge lumen 15 is designated 25 while the inlet aperture of intake lumen 20 is designated 35.

Figure 7:
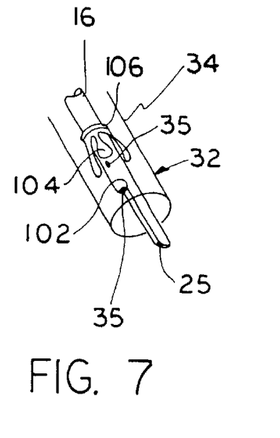
FIG. 7 is an enlarged view of the in situ enlarged end of a sinuous tubular member forming a part of a catheter embodying aspects of the invention.

In the embodiment illustrated in FIG. 7, means for separating inlet aperture 35 from vessel wall 34 are provided in part by a step 102 formed transversely to the axis of elongation of tubular member 16 where intake aperture 35 sits within step 102 and faces axially. In the embodiment illustrated in FIG. 7 means for separating tubular member aperture 35 from wall 34 is further provided by a circumferentially spaced collection of petal-like enlargement structures 104 which are connected about a central collar 106 and fixed about tubular member 16. Petals 104 extend somewhat radially outwardly respecting collar 106 and may contact the cylindrical interior of wall 34 thereby to separate wall 34 from intake aperture 35. Petals 104 are preferably unitarily formed of plastic together with collar 106 and are resiliently biased outwardly respecting the axis of tubular member 16 so that the radially outer extremities of petals 104 are well outboard of as intake aperture 35. Two intake apertures 35 are provided in the embodiment illustrated in FIG. 7.

In the embodiment illustrated in FIG. 10 again two intake apertures 35 are provided. The embodiment of FIG. 10, like the embodiment of FIG. 7, utilizes a step construction with step 102 extending transversely respecting the longitudinal axis of tubular member 16 and one of intake apertures 35 formed in step 102. A second intake aperture 35 is formed in the cylindrical outwardly facing surface of tubular member 16. An embodiment illustrated in FIG. 10, the means for separating inlet aperture 35 from vessel wall 34 is further provided by a collection of elongated leaf members 108 which extend between two collars 106 and are formed of generally flattened, broad strands of plastic with leaf members 108 having effective width, measured transversely respecting vessel 32 to define a circumferential outer extremity of tubular member 16 which is outboard of immediately adjacent inlet orifice 35. Hence, vessel wall 34 would first contact a lateral portion of leaf member 108 and not clog or cover aperture 35.

FIG. 11 illustrates a variation of the structure shown in FIG. 10 where leaf members 108 have been radially outwardly bowed to provide even greater separation of vessel wall from aperture 35 which adjacent to one of the two enlargement collars 106 between which leaf members 108 extend.

Figure 12:
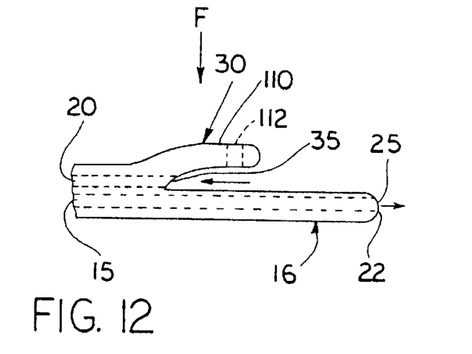
FIG. 12 is a partially sectioned side elevation of a tip extremity of a tubular member part of a catheter embodying aspects of the invention.
Figure 13:
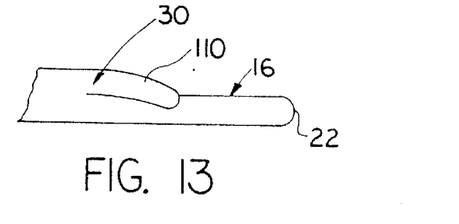
FIG. 13 is a side elevation of the structure illustrated in FIG. 12 showing the vessel separating means in a deformed condition.

In FIG. 12 means 30 for separating tubular member 20 intake aperture 35 from vessel wall 34 is provided by a cantilever finger member 110 which extends somewhat radially outwardly from a central portion of tubular member 16 and longitudinally along tubular member 16 to overly aperture 35. Cantilever finger member 110 is resiliently deformable so that upon force applied to finger member 110 in the direction indicated generally by arrow F in FIG. 12, finger member 110 deforms downwardly considering FIG. 12 to the position illustrated in FIG. 13, thereby covering inlet aperture 35 and presenting the intake of debris thereby. When such force is relieved, cantilever finger member 110 resiliently returns to its position illustrated in FIG. 12 thereby opening aperture 35 yet preventing aperture 35 from encountering wall 34 of vessel 32 within which tubular member 16 is resident.

Figure 14:
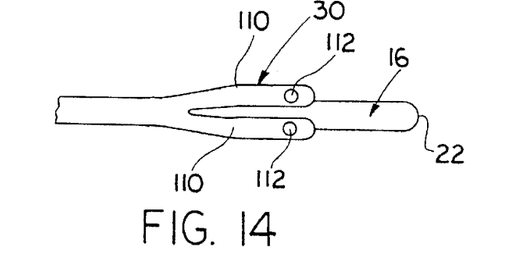
FIG. 14 is a top view of the structure illustrated in FIG. 12.
Figure 15:
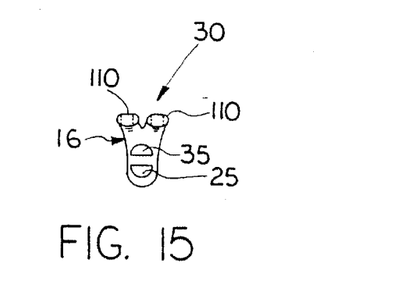
FIG. 15 is a side elevation of the structure illustrated in FIG. 12.

Preferably a pair of cantilever finger members 110 is provided as is apparent from FIGS. 14 and 15.

Optionally, apertures 112 may be provided in finger members 110 to provide maximum access of fluid flow within vessel 32 to intake aperture 35.

Figure 16:
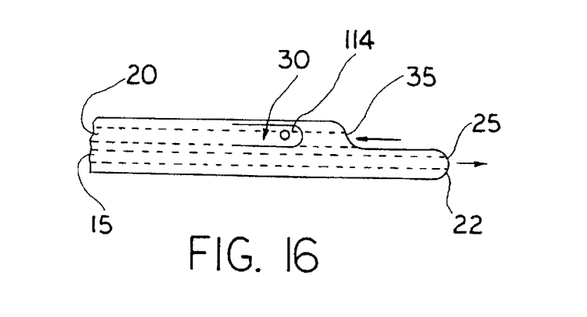
FIG. 16 is a side elevation of a second embodiment of a tip with vessel separating means at an extremity of the tubular member forming a part of the catheter of the invention.
Figure 17:
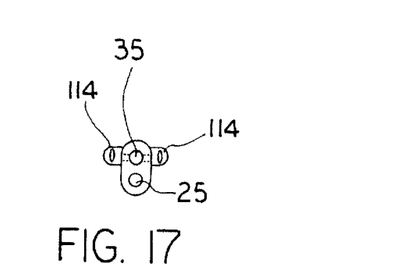
FIG. 17 is an end view of the structure illustrated in FIG. 16.
Figure 18:
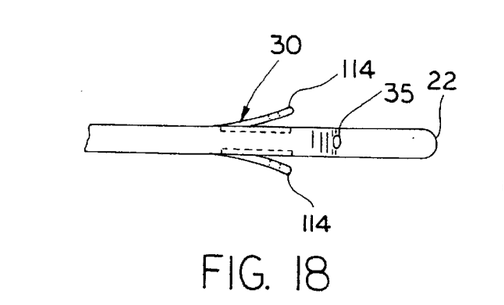
FIG. 18 is a top view of the structure illustrated in FIG. 16.
Figure 19:
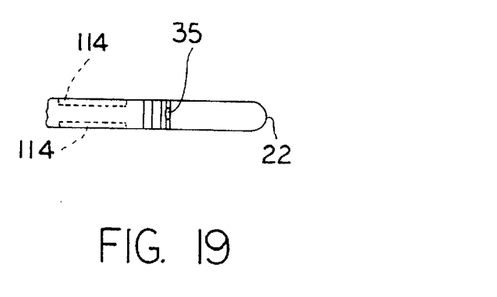
FIG. 19 is a top view of the structure illustrated in FIG. 16 with the vessel separating means in a deformed, compressed condition.
Figure 20:
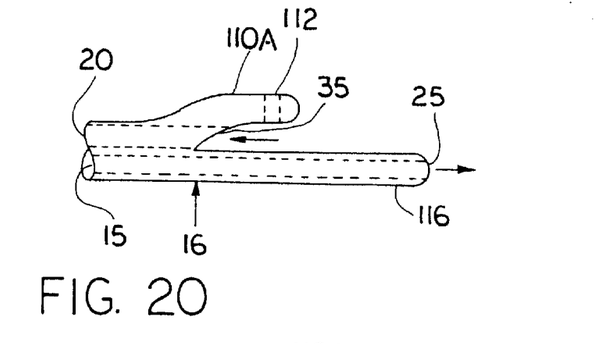
FIG. 20 is a side elevation of a third embodiment of a tip with vessel separating means at an extremity of the tubular member forming a part of the catheter of the invention.
Figure 21:
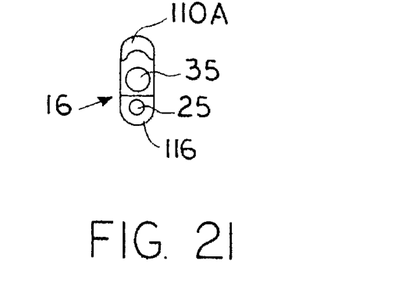
FIG. 21 is an end view of the structure illustrated in FIG. 20.
Figure 22:
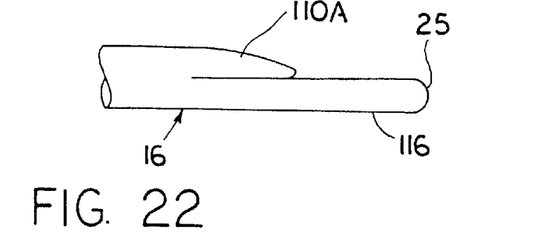
FIG. 22 is a view similar to FIG. 20 but showing the vessel separation means in a deformed condition.
Figure 23:
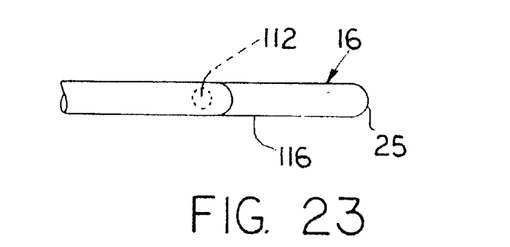
FIG. 23 is a top view of the structure illustrated in FIGS. 20 and 22.

In FIG. 16 means for separating tubular member 20 intake aperture 35 from vessel wall 34 is provided by a pair of outwardly biased flaps 114 which are preferably integrally formed from tubular member 16. Flaps 114 serving as the separating means extend outwardly beyond respective parallel sides of tubular member 16 and are resiliently deformable to within the periphery of tubular member 16 in response to force in such direction. The flap members extending radially outwardly beyond the periphery of the catheter is apparent from FIG. 18 with the flap members being resiliently deformed within the periphery of the tubular member as apparent from FIG. 19. In the position illustrated in FIG. 18, the flap members maintain tubular member 20 inlet aperture 35 spaced from vessel wall 34.

In every embodiment of the tip members particularly means for separating the tubular member 20 intake aperture 35 from vessel wall 34, tubular member 16 and tip portion thereof is free to move longitudinally within vessel 32. The separating means 30, no matter what their configuration, do not fix tubular member vis-avis the vessel in which the tubular member resides. This prevents trauma and stress to the vessel wall and reduces the possibility of build-up of thrombolytic material in the vicinity of inlet aperture 35.

The preferred cross-sectional configuration of tubular member 16 is illustrated in FIGS. 5 and 6 where the periphery of tubular member 16 includes a pair of parallel side segments each designated 44 connected by a pair of semi-circular arc segments each designated 46. An internal web 48 separates intake lumen 20 from discharge lumen 15.

In the embodiments illustrated in FIGS. 12 through 23 tubular member 16 includes a rounded distal end 22 in addition to a rounded lateral outer periphery 18 defined by the two arc segments 46 and connecting parallel segments 44.

FIGS. 20 through 23 depict another embodiment of means for separating tubular member 20 intake aperture 35 from vessel wall 34 which is similar to the structure illustrated in FIGS. 12 through 15. In FIGS. 20 through 23 a cantilever finger member 110A extends somewhat radially outwardly from the remaining portion of tubular member 16 and axially longitudinally with respect to intake aperture 35. In the embodiment illustrated in FIGS. 20 through 23, upon a resilient deformation of cantilever finger member 110A, that member deforms against a remaining axially elongated portion of tubular member 16, closing aperture 35 and presenting any influx thereinto of debris. This is not unlike the structure illustrated in FIGS. 12 through 15, where there are two cantilever finger members 110 which fold on either side of the remaining longitudinally extending portion 116 of tubular member 16. Similarly to the structure illustrated in FIGS. 12 through 15, the embodiment of FIGS. 20 through 23 may optionally include an auxiliary aperture 112 in cantilever finger member 110 to minimize resistance of flow to aperture 35 of inflow lumen 20. In the embodiments illustrated all edges and external surfaces of tubular member 16 are rounded or flat; there are no sharp edges.

Figure 24:
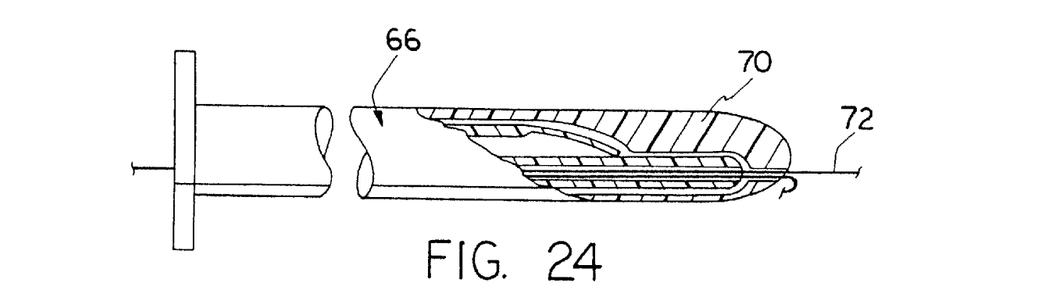
FIG. 24 is a partially sectioned view of the tip portion of the tubular means part of a catheter embodying the invention packaged in a peelaway sheath together with a protective nose cone and in position on a wire for unitary delivery and implantation into a patient.
Figure 25:
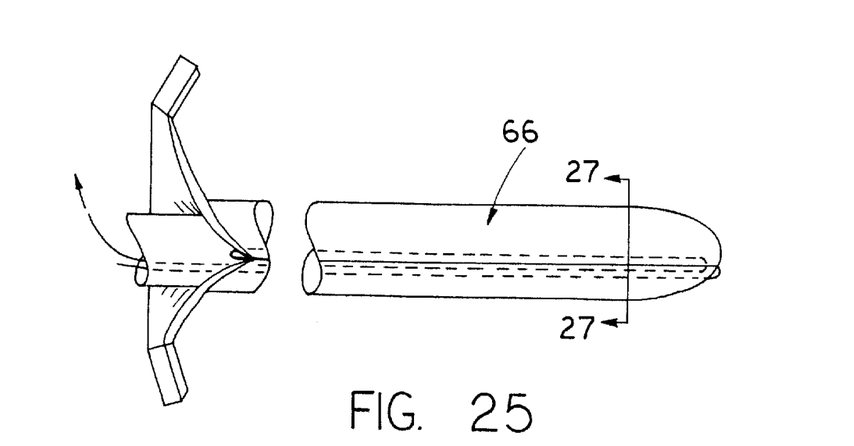
FIG. 25 is a view of the structure illustrated in FIG. 24 showing the peelaway nature of the sheath.
Figure 26:
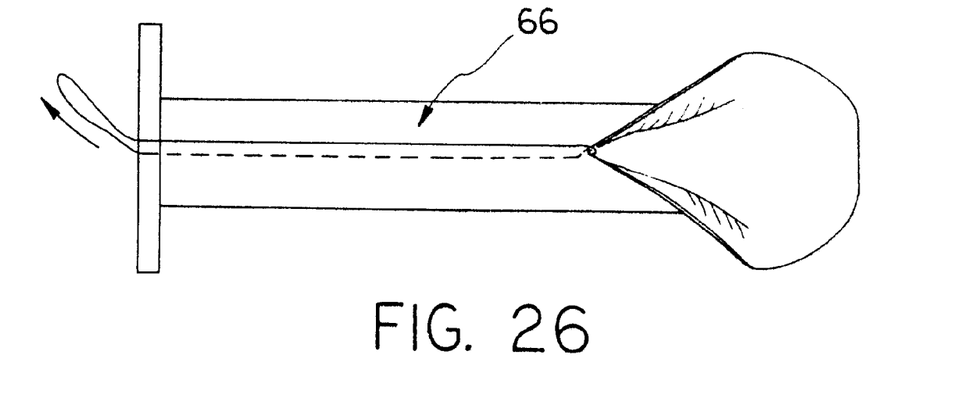
FIG. 26 is a view of a variation of the structure illustrated in FIG. 24 showing the sheath peeling from the opposite end.
Figure 27:
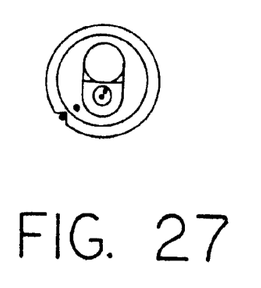
FIG. 27 is a sectional view of the catheter and sheath taken at lines and arrows 27—27 in FIG. 25.
Figure 28:
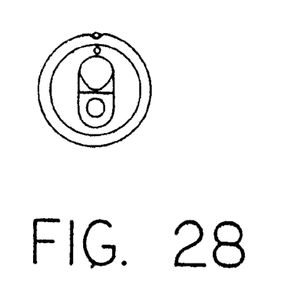
FIG. 28 is an end view of the catheter and sheath shown in FIG. 26.

FIGS. 24 and 25 depict catheter 10 in accordance with the invention equipped with an optional peelaway sheath designated generally 66 together with a protective auxiliary nose cone 70 overlying the rounded distal end 22 of tubular member 16 within sheath 66. In FIG. 24 catheter 10 overlying protective nose cone 70 and sheath 66 is depicted on a guide wire 72 in configuration to be implanted within a patient of interest. The wire 72 is similarly depicted in FIG. 1. Sheath 66 together with protective nose cone 70 facilitate installation of the catheter 10 in a patient. For such procedure, the surgeon initially inserts a wire 72 using a dilator into the patient. The catheter 10, having protective nose cone 70 in place thereover and sheath 66 encasing nose cone 70 and catheter 10 is then fed along guide wire 72 and positioned, preferably using x-ray or radiographic guidance, in the appropriate lumen in the human body. Once the catheter is in the appropriate position, a ripcord 68 may be pulled, thereby causing sheath 66 to rent, permitting sheath 66 to be withdrawn from the patient and leaving catheter 10 in place. Protective nose cone 70 is configured to fit over distal end of catheter 10 and particularly to fit over the distal end configuration chosen for the particular catheter application.

The sheath aspect of the invention provides a surgical apparatus capable of transcutaneously traversing from a first percutaneous location to a second subcutaneous location.

The separable sheath preferably includes an embedded suture adjusted to separate opposing wall sections along a longitudinal suture path formed in the sheath material such that the sheath may be split along the line by removing the suture and removed from the transcutaneous channel subsequent to the passage of a desired device.

Referring to FIGS. 29 through 33, the separable sheath is generally designated 66. The separable sheath preferably includes a cylindrical conduit 120 having a distal end 140 and proximal end 160, a longitudinal line of weakness 300 and flange portions 180 and 220 formed about proximal end 160 of conduit 120. Flange portions 180 and 220 maintain the percutaneous position of proximal end 160. Flange tabs 180 and 220 position sheath 66 in the transcutaneous pathway such that the sheath does not advance into tissue too deeply. A line of weakness 300 runs along the length of conduit 120 such that upon separating conduit wall flange tabs 220 and 180 separate along line 300.

Figures 29, 30:
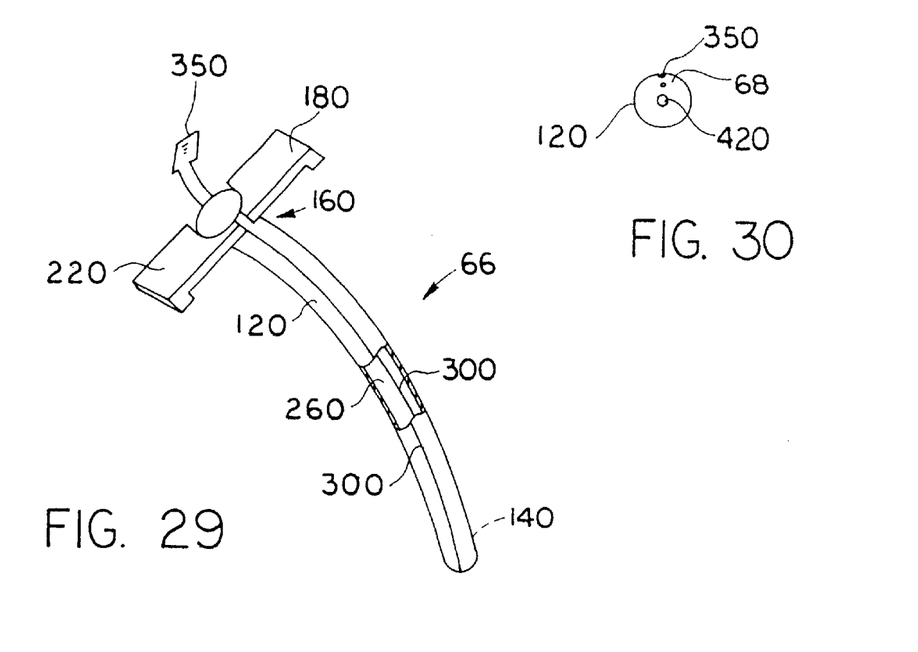
FIG. 29 shows a separable surgical sheath.
FIG. 30 is a sectional view of the sheath.
Figure 31:
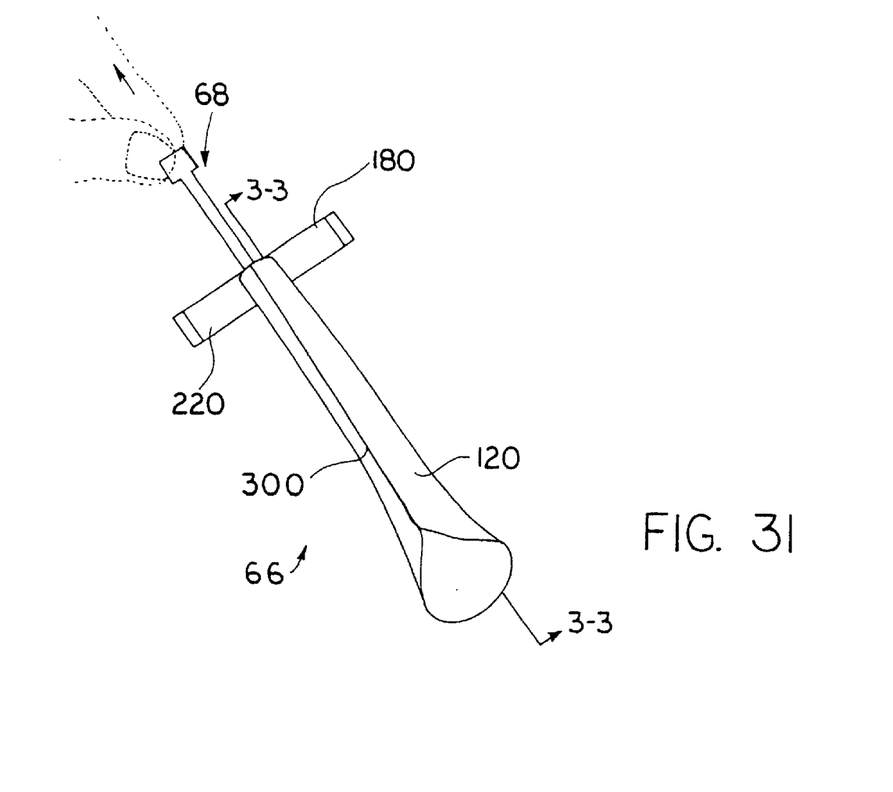
FIG. 31 shows the sheath of FIG. 29 with its proximal end separated by the embedded suture.

The separable sheath includes an interior axially lumen extending from distal end 140 to proximal end 160. The distal end 140 accesses a subcutaneous location; proximal end 160 is positioned at a percutaneous location.

The sheath is desirably transcutaneously positioned to provide access for surgical apparatus such as catheter 10 to a subcutaneous location. Typically, the sheath is introduced through a transcutaneous access channel provided by an incision or needle path and advanced over a guide wire 72 to the subcutaneous site of interest by threading the guide wire through nose cone 70 by way of cone tip aperture 420. The cone shaped tip of conduit 120 dilates the transcutaneous pathway as it is advanced therethrough.

The elongated portion of sheath 66 is cylindrical and preferably formed of thin plastic such as polyethylene, fluorinated ethylene-propylene or like plastic materials employed in medical applications. In the embodiments shown in FIGS. 29 through 33, a suture 350 is preferably embedded along the longitudinal length of the conduit wall defining a line of weakness 300 along the length of conduit 120 portion of sheath 66. Pulling a free end or "ripcord" 68 of the suture 350 away from the wall separates the conduit wall along the line of weakness 300. In this way, the conduit 120 may be split to facilitate retrieval of the conduit 120 portion of the sheath from the transcutaneous pathway. The embedded suture 350 may be formed within conduit 120 to provide a stress concentration area on either the distal or proximate end to facilitate rupture of conduit 120 in a predetermined direction.

Figure 32:
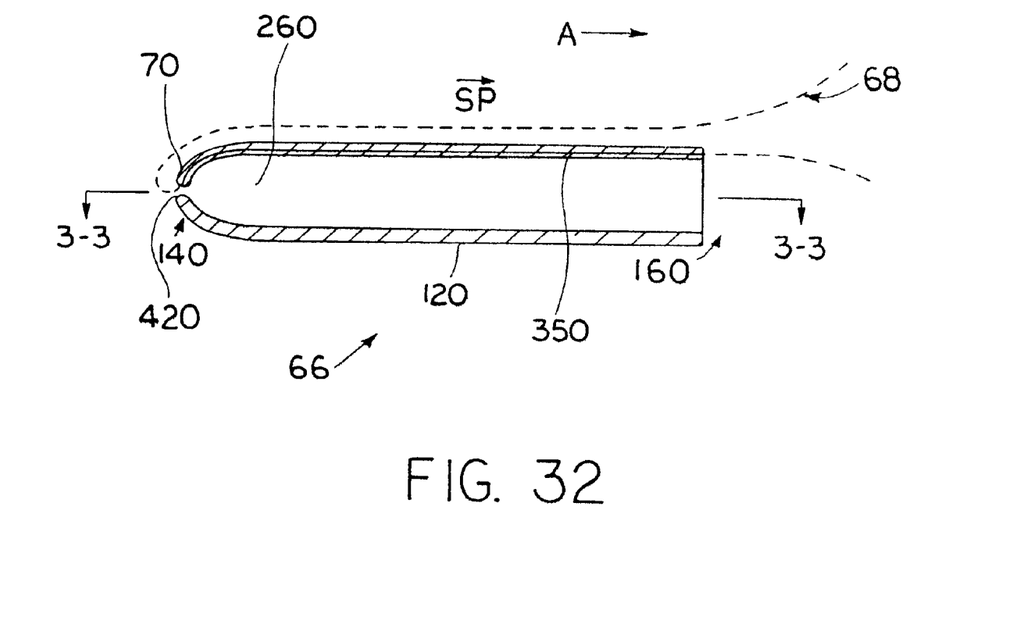
FIG. 32 shows a side section of the sheath conduit tube and embedded suture configured to rupture from the distal to proximate end as show in FIG. 31.
Figure 33:
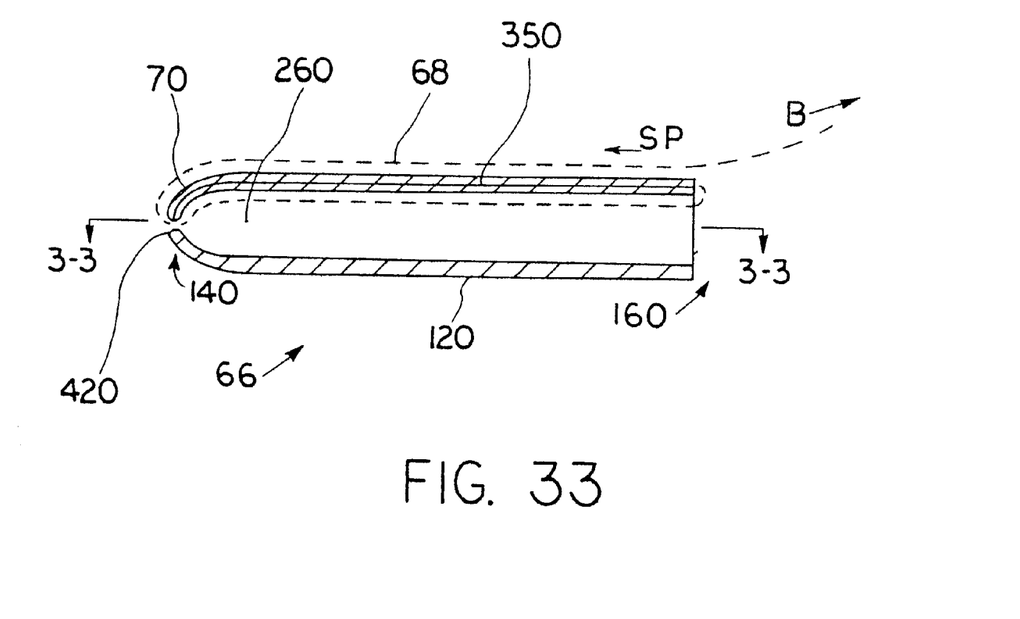
FIG. 33 shows a side section of the sheath conduit tube and embedded suture configured to rupture from the proximate end to the distal end.

In the embodiment shown in FIGS. 32 and 33, the embedded suture 350 defines a weakened section of the conduit wall such that pulling the suture away from the wall separates the conduit wall along the line of weakness. As shown in FIG. 32, the suture 350 is preferably embedded from proximal end 160 of the conduit 120 downwardly to distal end 140 of the conduit 120, with a free end of the suture 68 preferably looping at and around distal end 140 upwardly, and back towards the proximal 160. In this way, separation is effectuated using the free end of suture 68 which is maintained at a percutaneous location i.e., distal end 140 of conduit 120. Drawing ripcord 68 upwardly, away from distal end 140 as denoted by arrow "A", causes conduit 12 to rupture along the longitudinal suture path in the direction indicated by arrow "SP" from distal to proximate direction such that the sheath 66 may be removed from its transcutaneous position as illustrated in FIG. 32.

Alternatively, suture 350 may be configured to rupture the conduit wall beginning with proximate end 160 and proceeding toward distal end 140 as shown in FIG. 33, depending on the position of suture free end 68. As shown in FIG. 33, suture 35 is embedded from proximal end 160 of conduit 120 downwardly to distal end 140, with a free end of suture 68 looping at proximate end 160 downwardly through lumen 260 to distal end 140 where it again loops upwardly to proximate end 160, extending along the outside surface of conduit 120. In this way, separation effectuated by the free end of suture 68 which extends upwardly though lumen 260 and is maintained at a percutaneous location, i.e. distal end 140 of the conduit. Drawing the suture upwardly, away from distal end 140, as indicated by arrow "B", causes conduit 120 to rupture along the suture path from proximate end 160 of conduit 120. In this embodiment, suture 350 ruptures from proximate to distal as denoted by the arrow "SP" such that the sheath 66 may be removed from its transcutaneous position.

Once the sheath is positioned in the transcutaneous pathway surrounding any associated instrumentation, the sheath is removed and the instrument(s) within deployed. The sheath is removed from the transcutaneous pathway by rupturing embedded suture 350 along the line of weakness defined by the embedded suture.

I claim the following:

1. A stationary central dialysis catheter comprising:
   a. a planar axially elongated sinuous tubular member having a plurality of axially extending lumens therein;
   b. at least a part of said tubular member having predetermined two-dimensional shape substantially matching an anatomical central tunnel region of interest, including at least two portions of relative straightness connected by a curved portion region, to fit a preselected body lumen in said anatomical region of interest;
   c. said tubular member being deformable and resiliently returning to said predetermined two-dimensional shape after deformation;
   d. in said part of said tubular member having predetermined shape at least two of said lumens each having at least one aperture for through passage of fluid during dialysis, said apertures being axially displaced from one another along said tubular member;
   e. a flexible sheath having a proximal portion and a distal portion and complementally surrounding at least said part having predetermined two-dimensional shape, for protecting said tubular member part having predetermined shape, and being peelably removable therefrom in situ when said tubular member has been positioned within said preselected lumen;
   f. ripcord means in the form of a suture embedded in said flexible sheath and running the longitudinal length thereof to define a line of weakness therein, the suture looped around at the distal portion with free ends at the proximal portion to define the line of weakness separable first adjacent the suture loop, the suture extending along the length of said tubular member for rupturing said sheath in a proximal direction in the vicinity of an axial extremity of said tubular member proximate said apertures in response to manual force applied to a portion of said ripcord extending from the body of a patient in whom said catheter has been implanted.

2. The catheter of claim 1 wherein said ripcord is embedded into said tubular member wall.

3. The catheter of claim 1 wherein said ripcord is inside of said sheath.

4. The catheter of claim 1 wherein said ripcord is embedded into said sheath.

5. A stationary central dialysis catheter comprising:
   a. a planar axially elongated sinuous tubular member of integral construction having a plurality of axially extending lumens formed therein and a generally rounded smooth outer periphery;
   b. at least two of said lumens each having at least one aperture for through passage of fluid during dialysis, said apertures being axially displaced from one another along said tubular member and proximate one end of said tubular member, said tubular member being straight between said apertures in said respective lumens;
   c. at least a part of said tubular member being of predetermined two-dimensional generally M-shape substantially matching human left side venous anatomy, including portions of relative straightness connected by curved portions, fitting a preselected body lumen in said anatomical region of interest;
   d. said tubular member having predetermined two-dimensional shape substantially matching an anatomical central tunnel region of interest, including at least two portions of relative straightness connected by a curved portion region, to fit a preselected body lumen in said anatomical region of interest;
   e. said tubular member being deformable and resiliently returning to said predetermined two-dimensional shape after deformation;
   f. said tubular member including means normally biased away from the member for separating said tubular member aperture remote from said end from a surrounding wall of said preselected body lumen when said catheter is in place therewithin while permitting axial movement of said tubular member within said lumen relative to said wall, said separating means being movable in a direction against the normal bias towards the tubular member to cover one of the apertures in the tubular member;
   g. said tubular member having wall thickness greater in the curved portion than in said portions of relative straightness.

6. A stationary central dialysis catheter comprising:
   a. a planar axially elongated sinuous tubular member of integral construction having a plurality of axially extending lumens formed therein and a generally rounded smooth outer periphery;
   b. at least two of said lumens each having at least one aperture for through passage of fluid during dialysis, said apertures being axially displaced from one another along said tubular member and proximate one end of said tubular member;
   c. at least a part of said tubular member being of predetermined two-dimensional generally M-shape substantially matching human left side venous anatomy, including portions of relative straightness connected by curved portions, fitting a preselected body lumen in said anatomical region of interest;
   d. said tubular member having predetermined two-dimensional shape substantially matching an anatomical central tunnel region of interest, including at least two portions of relative straightness connected by a curved portion region, to fit a preselected body lumen in said anatomical region of interest;
   e. said tubular member being deformable and resiliently returning to said predetermined two-dimensional shape after deformation;
   f. said tubular member including non-inflatable means for separating said tubular member aperture remote from said end from a surrounding wall of said preselected body lumen when said catheter is in place therewithin while permitting axial movement of said tubular member within said lumen relative to said wall, said non-inflatable means being normally biased away from the tubular member and movable to its biased position without any actuation by the user;
   g. said tubular member having wall thickness greater in the curved portion than in said portions of relative straightness;
   h. a flexible sheath having a proximal portion and a distal portion and complementally surrounding at least said part having predetermined two-dimensional shape, for protecting said tubular member part having predetermined shape, and being peelably removable therefrom in situ when said tubular member has been positioned within said preselected lumen;
   i. ripcord means in the form of a suture embedded in said flexible sheath and running the longitudinal length thereof to define a line of weakness therein, extending along said tubular member for rupturing said sheath in the vicinity of an axial extremity of said tubular member proximate said apertures in response to manual force applied to a portion of said suture extending from the body of a patient in whom said catheter has been implanted.

7. A stationary central dialysis catheter comprising:
   a. a planar axially elongated sinuous tubular member of integral construction having a plurality of axially extending lumens formed therein and a generally rounded smooth outer periphery;
   b. at least two of said lumens each having at least one aperture for through passage of fluid during dialysis, said apertures being axially displaced from one another along said tubular member and proximate one end of said tubular member, said tubular member being straight between said apertures in said respective lumens;
   c. at least a part of said tubular member being of predetermined two-dimensional generally M-shape substantially matching human left side venous anatomy, including portions of relative straightness connected by curved portions, fitting a preselected body lumen in said anatomical region of interest;
   d. said tubular member being deformable and resiliently returning to said predetermined two-dimensional shape after deformation;
   e. said tubular member including means for separating said tubular member aperture remote from said end from a surrounding wall of said preselected body lumen when said catheter is in place therewithin while permitting axial movement of said tubular member within said lumen relative to said wall;
   f. said tubular member having wall thickness greater in the curved portion than in said portions of relative straightness;

g. a flexible sheath having a proximal portion and a distal portion and complementally surrounding at least said part having predetermined two-dimensional shape, for protecting said tubular member part having predetermined shape, and being peelably removable therefrom in situ when said tubular member has been positioned within said preselected lumen;

h. ripcord means in the form of a suture embedded in said flexible sheath and running the longitudinal length thereof to define a line of weakness therein, the suture looped around at the distal portion with free ends at the proximal portion to define the line of weakness separable first adjacent the suture loop, the suture extending along said tubular member for rupturing said sheath in a proximal direction in the vicinity of an axial extremity of said tubular member proximate said apertures in response to manual force applied to a portion of said suture extending from the body of a patient in whom said catheter has been implanted.

8. A stationary central dialysis catheter comprising:

a. a planar axially elongated sinuous tubular member of integral construction having a plurality of axially extending lumens formed therein and a generally rounded smooth outer periphery;

b. at least two of said lumens each having at least one aperture for through passage of fluid during dialysis, said apertures being axially displaced from one another along said tubular member and proximate one end of said tubular member, said tubular member being straight between said apertures in said respective lumens;

c. said tubular member having predetermined two-dimensional shape substantially matching an anatomical central tunnel region of interest, including at least two portions of relative straightness connected by a curved portion region, to fit a preselected body lumen in said anatomical region of interest;

d. said tubular member being deformable and resiliently returning to said predetermined two-dimensional shape after deformation;

e. said tubular member including elongate flexible means normally biased away from the member for separating said tubular member aperture remote from said end from a surrounding wall of said preselected body lumen when said catheter is in place therewithin while permitting axial movement of said tubular member within said lumen relative to said wall, said flexible means being normally biased away from the tubular member and movable to its biased position without any actuation by the user.

9. The catheter of claim 8 wherein said tubular member has generally oval cross-section.

10. The catheter of claim 9 wherein said oval has a pair of parallel sides connected by opposed semicircular arc segments.

11. The catheter of claim 8 wherein said separating means extends outwardly beyond one of said arc segments.

12. The catheter of claim 10 wherein said separating means extends outwardly beyond one of said portions of relative straightness.

13. The catheter of claim 12 wherein said separating means extends from one of said arc segments outwardly beyond both of said parallel sides.

14. The catheter of claim 8 wherein said separating means extends radially outwardly beyond the periphery of said catheter.

15. The catheter of claim 14 wherein said separating means is resiliently deformable to within said periphery of said tubular member.

16. The catheter of claim 8 wherein said apertures are first apertures defining terminus of respective lumens within said tubular member and generally radially facing apertures in said separating means faciliate fluid communication from the surrounding vessel with said lumen terminating at said first aperture which is remote from said end.

17. The catheter of claim 8 wherein said lumens are separated by a transversely extending web within said tubular member and said web forms a portion of the exterior of said tubular member intermediate said apertures.

18. The catheter of claim 8 wherein said separating means further comprises a flange extending axially from said tubular member transversely spaced from and generally parallel with a web part forming a portion of the exterior of said tubular member.

19. The catheter of claim 8 wherein said separating means further comprises an axially elongated flange extending laterally from said parallel side of said tubular member.

20. The catheter of claim 8 wherein said separating means further comprises a flange extending axially from said tubular member transversely spaced from and generally parallel with a web part forming a portion of, the exterior of said tubular member.

21. The catheter of claim 8 wherein said separating means further comprises at least one rib extending radially from said tubular member adjacent said tubular member aperture remote from said end.

22. The catheter of claim 8 wherein said aperture more proximate said end faces axially.

23. A stationary central tunnel dialysis catheter comprising:

a. a planar axially elongated sinuous tubular member having a plurality of axially extending lumens therein;

b. at least two of said lumens each having at least one aperture for through passage of fluid during dialysis, said apertures being axially displaced from one another along said tubular member, said tubular member being straight between said apertures in said respective lumens;

c. said tubular member having predetermined two-dimensional shape substantially matching an anatomical central tunnel region of interest, including at least two portions of relative straightness connected by a curved portion region, to fit a preselected body lumen in said anatomical region of interest;

d. said tubular member being deformable and resiliently returning to said predetermined two-dimensional shape after deformation;

e. said tubular member having an outer diameter greater in the curved portion than in the portions of relative straightness such that the wall thickness is greater in the curved portion than in said portions of relative straightness.

24. The catheter of claim 23 wherein said tubular member is resiliently deformable into an essentially straight line configuration.

25. The catheter of claim 23 wherein said tubular member wall thickness is greater at an outer part of said curved portion than at a corresponding inner part of said curved portion.

26. A stationary central tunnel dialysis catheter comprising:

a. sinuous tubular member having a plurality of axially extending lumens formed therein;

b. at least two of said lumens each having at least one aperture for through passage of fluid during dialysis, the apertures being axially displaced from one another along the tubular member;

c. at least a portion of the tubular member having a predetermined shape substantially matching an anatomical portion of a patient;

d. a removable flexible sheath surrounding at least a portion of the tubular member for protecting the tubular member, the sheath being separable from the tubular member and having a proximal portion and a distal portion; and e. a suture associated with the sheath and extending longitudinally along the sheath from a proximal portion to a distal portion, the suture being pulled from a proximal end to separate the sheath along a line of weakness formed by the suture, the suture being connected to the distal portion of the sheath to define a line of weakness separable first at the distal portion adjacent the connection separating progressively the sheath in a direction from the distal portion of the sheath toward the proximal portion of the sheath to separate the sheath from the tubular member for removal from the body.

27. A stationary central tunnel dialysis catheter comprising:

a. a sinuous tubular member having a plurality of axially extending lumens formed therein and having an outer diameter;

b. at least two of said lumens each having at least one aperture for through passage of fluid during dialysis, the apertures being axially displaced from one another along the tubular member;

c. at least a portion of the tubular member having a predetermined shape substantially matching an anatomical portion of a patient;

d. a movable flexible elongated member extending from the tubular member, the elongated member being biased away from the tubular member and movable from a first position closer to the tubular member to a second fully biased position biased away from the tubular member without any actuation by the user to maintain separation of at least one of the apertures from the wall of the vessel, the flexible elongated member having an outer diameter wherein in its fully biased position, the outer diameter of the elongated member and the outer diameter of tubular member, in combination, is less than the outer diameter of vessel in which it is inserted to allow unobstructed axial movement of the tubular member.

28. The catheter of claim 27 wherein the elongated member is a first finger like member having a longitudinal axis substantially parallel with a longitudinal axis of the tubular member.

29. The catheter of claim 28, further comprising a second finger like member radially displaced from the first finger like member.

30. The catheter of claim 27 wherein movement of the first finger like member to the second position blocks at least one of the apertures.

* * * * *